US009896649B2

(12) United States Patent
Dihora et al.

(10) Patent No.: US 9,896,649 B2
(45) Date of Patent: Feb. 20, 2018

(54) BENEFIT AGENT DELIVERY COMPOSITION WITH A LOW CONTENT OF SHELL PARTICLES

(71) Applicant: APPVION, INC., Appleton, WI (US)

(72) Inventors: Jiten Odhavji Dihora, Hamilton, OH (US); Walter Franciscus Joanna Vanderveken, Wilrijk (BE); Sanford Theodore Kirksey, Jr., Cincinnati, OH (US); John Charles DeBraal, Appleton, WI (US); Robert Stanley Bobnock, Menasha, WI (US); Adam Keith Druckrey, Appleton, WI (US); Gary Thomas Hart, Hortonville, WI (US)

(73) Assignee: ENCAPSYS, LLC, Appleton, WI (US)

(*) Notice: Subject to any disclaimer, the term of this patent is extended or adjusted under 35 U.S.C. 154(b) by 65 days.

(21) Appl. No.: 14/547,896

(22) Filed: Nov. 19, 2014

(65) Prior Publication Data

US 2015/0080285 A1   Mar. 19, 2015

Related U.S. Application Data

(62) Division of application No. 12/508,214, filed on Jul. 23, 2009, now Pat. No. 8,974,547.

(60) Provisional application No. 61/084,786, filed on Jul. 30, 2008.

(51) Int. Cl.

| *C11D 3/50* | (2006.01) |
|---|---|
| *C11D 17/00* | (2006.01) |
| *A01N 25/26* | (2006.01) |
| *A61K 8/11* | (2006.01) |
| *A61Q 19/00* | (2006.01) |
| *B01J 13/20* | (2006.01) |
| *C11D 3/00* | (2006.01) |
| *D06M 13/00* | (2006.01) |
| *D06M 23/12* | (2006.01) |
| *A01N 25/00* | (2006.01) |
| *C11B 9/00* | (2006.01) |
| *A61K 8/84* | (2006.01) |
| *A61K 9/00* | (2006.01) |
| *A61K 9/08* | (2006.01) |
| *A61Q 13/00* | (2006.01) |
| *A61Q 5/02* | (2006.01) |
| *A61Q 19/10* | (2006.01) |

(52) U.S. Cl.
CPC .............. *C11D 3/505* (2013.01); *A01N 25/00* (2013.01); *A01N 25/26* (2013.01); *A61K 8/11* (2013.01); *A61K 8/84* (2013.01); *A61Q 19/00* (2013.01); *B01J 13/20* (2013.01); *C11B 9/00* (2013.01); *C11D 3/001* (2013.01); *C11D 17/0039* (2013.01); *D06M 13/005* (2013.01); *D06M 23/12* (2013.01); *A61K 9/0014* (2013.01); *A61K 9/08* (2013.01); *A61K 2800/412* (2013.01); *A61Q 5/02* (2013.01); *A61Q 13/00* (2013.01); *A61Q 19/10* (2013.01)

(58) Field of Classification Search
None
See application file for complete search history.

(56) References Cited

U.S. PATENT DOCUMENTS

| 4,203,837 | A | 5/1980 | Hoge et al. | |
|---|---|---|---|---|
| 5,288,632 | A | 2/1994 | Pannell | |
| 5,705,222 | A * | 1/1998 | Somasundaran | ........ B01J 13/02 427/220 |
| 5,948,441 | A | 9/1999 | Lenk et al. | |
| 2004/0140374 | A1 | 7/2004 | Snyder et al. | |
| 2005/0129946 | A1* | 6/2005 | Hayashi | ................... B01J 13/02 428/402.2 |
| 2006/0065605 | A1 | 3/2006 | Kirker et al. | |
| 2006/0248665 | A1* | 11/2006 | Pluyter | .................... A61K 8/11 8/406 |
| 2007/0149424 | A1 | 6/2007 | Warr et al. | |
| 2007/0191256 | A1* | 8/2007 | Fossum | .................... C11D 1/62 510/515 |
| 2007/0202063 | A1* | 8/2007 | Dihora | ..................... A61K 8/11 424/70.1 |
| 2007/0275866 | A1 | 11/2007 | Dykstra | |
| 2008/0031961 | A1* | 2/2008 | Cunningham | ........... A61K 8/11 424/489 |
| 2009/0258042 | A1* | 10/2009 | Anastasiou | .............. A61K 8/11 424/401 |

FOREIGN PATENT DOCUMENTS

WO     WO 92/18601 A1    10/1992

OTHER PUBLICATIONS

EWG's Skin Deep® Cosmetics Database "Paraffin" page, accessed online on Mar. 31, 2016, web address: http://www.ewg.org/skindeep/ingredient/704453/PARAFFIN/, copy attached to the case file as a PDF.*

EWG's Skin Deep® Cosmetics Database "Paraffin", web address: http://www.ewg.org/skindeep/ingredient/704453/PARAFFIN/; the Wayback Machine shows that the Skin Deep reference was available on Jan. 7, 2012, PDF copy attached.*

(Continued)

*Primary Examiner* — Katie L Hammer
(74) *Attorney, Agent, or Firm* — K&L Gates LLP

(57) ABSTRACT

The present application relates to encapsulated benefit agents, compositions comprising such encapsulated benefit agents and processes for making and using compositions comprising such encapsulated benefit agents that do not require or require a reduced amount of scavenger materials. Such encapsulated benefit agents, compositions comprising such encapsulated benefit agents are processed such that no or lower levels of scavenger materials are required.

17 Claims, No Drawings

(56) References Cited

OTHER PUBLICATIONS

"Centrifugal Separations", Chapter 9 of Coulson and Richardson's, Chemical Engineering vol. 2—Particle Technology and Separation Process, 5th edition, copyright 2002, accessed online Jul. 27, 2011, pp. 475-476.
Champagne et al., "Microencapsulation for the improved delivery of bioactive compounds into foods", Current Opinion in Biotechnology, 2007, vol. 18, pp. 184-190.

* cited by examiner

BENEFIT AGENT DELIVERY COMPOSITION WITH A LOW CONTENT OF SHELL PARTICLES

CROSS REFERENCE TO RELATED APPLICATIONS

This application is a division of co-pending application Ser. No. 12/508,214 filed Jul. 23, 2009, which claims priority from U.S. Provisional Application Ser. No. 61/084,786 filed Jul. 30, 2008, the entire contents of each of which are hereby incorporated herein by reference.

FIELD OF INVENTION

The present application relates to encapsulated benefit agents, compositions comprising such encapsulated benefit agents and processes for making and using compositions comprising such encapsulated benefit agents.

BACKGROUND OF THE INVENTION

Benefit agents, such as perfumes, silicones, waxes, flavors, vitamins and fabric softening agents, are expensive and generally less effective when employed at high levels in personal care compositions, cleaning compositions, and fabric care compositions. As a result, there is a desire to maximize the effectiveness of such benefit agents. One method of achieving this objective is to improve the delivery efficiencies of such benefit agents. Unfortunately, it is difficult to improve the delivery efficiencies of benefit agents as such agents may be lost do to the agents' physical or chemical characteristics, or such agents may be incompatible with other compositional components or the situs that is treated.

In an effort to improve the delivery efficiencies of benefit agents, the industry, in many cases, encapsulated such benefit agents. Unfortunately, compositions such as melamine formaldehyde microcapsule slurries may contain materials such as residual formaldehyde that, to date, are removed by introducing scavenger materials into the slurry and/or products containing the aforementioned slurry. While such management efforts may be effective, such efforts increase formulation complexity as scavenger materials can be incompatible with many raw materials that are required to formulate a consumer desired product.

Accordingly, there is a need for encapsulated benefit agents, compositions, that do not require or require a reduced level of scavenger materials, and which comprise such encapsulated benefit agents and processes for making and using compositions comprising such encapsulated benefit agents.

SUMMARY OF THE INVENTION

The present application relates to encapsulated benefit agents, compositions comprising such encapsulated benefit agents and processes for making and using compositions comprising such encapsulated benefit agents that do not require or require reduced amounts of scavenger materials.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations there of.

As used herein, the phrase "benefit agent delivery particle" encompasses microcapsules including perfume microcapsules.

As used herein, the terms "particle", "benefit agent delivery particle", "capsule" and "microcapsule" are synonymous.

As used herein, the articles including "a" and "an" when used in a claim, are understood to mean one or more of what is claimed or described.

As used herein, the terms "include", "includes" and "including" are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Benefit Agent Delivery Compositions

Encapsulation processes typically transform two or more monomeric materials into one or more macromolecules that coat a benefit agent. During the encapsulation process undesirable by-products may be formed. For example, the condensation reaction of amino resins may generate formaldehyde. Attempts to remove such undesirable by-products include the employment of chemical scavengers. Applicants have surprisingly found that even when the residual by-products are managed by the aforementioned chemical means, there is a limit to which such by-products can be reduced and by-product levels may, over time, increase. Based on such observation, Applicants discovered that the encapsulation process yielded encapsulated benefit agents and shell particles comprising primarily the aforementioned macromolecules. In short, such shell particles may be essentially devoid of benefit agent, yet act as by-product reservoirs. Thus, when such shell particles are removed, by-product levels may be managed such that dramatically lower levels of by-product may be obtained and maintained.

Thus Applicants disclose a benefit agent delivery composition that may comprise, based on total benefit agent delivery composition weight:
  a.) from about 2% to about 95%, from about 20% to about 75%, from about 30% to about 70%, or even from about 30% to about 65%, of an encapsulated benefit agent, said encapsulated benefit agent optionally comprising a sufficient amount of benefit agent to provide, based on total benefit delivery composition weight from about 1% to about 85%, from about 8% to about 80%, from about 12% to about 75%, from about 15% to about 65%, from about 20% to about 60%, or even from about 25% to about 55% benefit agent;
  b.) less than from about 1% to about 30%, from about 1% to about 20%, from about 2% to about 20%, from about 5% to about 20%, from about 5% to about 15%, or even from about 5% to about 12% shell particles; and
  c.) the balance of said benefit agent delivery composition being one or processing aids and/or carriers.

In one aspect of the aforementioned benefit agent delivery composition said encapsulated benefit agent may comprise, a benefit agent selected from the group consisting of perfumes; brighteners; insect repellants; silicones; waxes; flavors; vitamins; fabric softening agents; skin care agents including paraffins; enzymes; anti-bacterial agents; bleaches; and mixtures thereof.

In one aspect of the aforementioned benefit agent delivery composition said shell particles may comprise an amino resin, for example a melamine and/or urea resin.

In one aspect of the aforementioned benefit agent delivery composition said perfume comprises a perfume raw material selected from the group consisting of Quadrant I, II, III perfume raw materials and mixtures thereof.

In one aspect of the aforementioned benefit agent delivery composition said one or more processing aids are selected from the group consisting of water, aggregate inhibiting materials such as divalent salts, soil suspending polymers, and mixtures thereof.

In one aspect of the aforementioned benefit agent delivery composition said one or more carriers may be selected from the group consisting of polar solvents, including but not limited to, water, ethylene glycol, propylene glycol, polyethylene glycol, glycerol; nonpolar solvents, including but not limited to, mineral oil, perfume raw materials, silicone oils, hydrocarbon paraffin oils, and mixtures thereof.

In one aspect of the aforementioned benefit agent delivery composition
  a. said perfume may comprise a perfume raw material selected from the group consisting of Quadrant I, II, III perfume raw materials and mixtures thereof;
  b. said one or more processing aids may be selected from the group consisting of water, aggregate inhibiting materials such as divalent salts, soil suspending polymers and mixtures thereof; and
  c. said one or more carriers may be selected from the group consisting of water, ethylene glycol, propylene glycol, polyethylene glycol, glycerol; nonpolar solvents such as mineral oil, perfume raw materials, silicone oils, hydrocarbon paraffin oils, and mixtures thereof.

In one aspect, Applicants disclose a benefit agent delivery composition made by any of the processes disclosed in the present specification.

Processes of Making Benefit Agent Delivery Compositions

In one aspect, Applicants disclose a process that may comprise subjecting an benefit agent delivery composition comprising one or more encapsulated benefit agents and greater than 0.9%, greater than 2.0%, greater than 5%, greater than 10% or even from greater than 10% to about 40% shell particles to an operation selected from the group consisting of centrifugation, filtration, solvent exchange, flash evaporation, decantation, flotation separation, spray drying, reactive adsorption, reactive absorption, and combinations thereof, for a sufficient period of time to reduce the percentage of said shell particles in said benefit agent delivery composition by at least 20%, at least 50%, at least 70%, at least 80%, at least 85%, at least 90%, at least 95% at least 99.9% or even from about 99.9% to about 99.999%.

In one aspect of the aforementioned process, said centrifugation may comprise a process selected from the group consisting of:
  a.) batch centrifugation that may comprise applying a centrifugal force in multiples of gravity of from about 100 to about 20,000 from about 200 to about 10,000, from about 300 to about 5,000, from about 500 to about 4,000, from about 1000 to about 3000 multiples of gravity to said benefit agent delivery composition, in another aspect, batch centrifugation that may comprise applying a centrifugal force in multiples of gravity of from about 100 to about 20,000 from about 200 to about 10,000, from about 300 to about 9,000, from about 500 to about 8,000, from about 2,000 to about 7,000 multiples of gravity to said benefit agent delivery composition;
b.) continuous centrifugation that may have at least one of the following process parameters; a centrifugal force in multiples of gravity of from about 100 to about 20,000 from about 200 to about 10,000, from about 300 to about 5,000, from about 500 to about 4,000, from about 1,000 to about 3,000 multiples of gravity to said benefit agent delivery composition; an inlet fluid viscosity of from about 0.1 to about 2000 centipoise, from about 1 to 500 centipoise, from about 10 to 100 centipoise; an inlet velocity of the benefit agent delivery composition of from about 0.2 to about 5 meters per second, from about 0.5 to about 5 meters per second, from about 1 to about 4 meters per second, or even from about 2 to about 3 meters per second; an the inlet pressure of the benefit agent delivery composition of from about 10 psig to about 120 psig, from about 20 psig to about 80 psig, from about 40 psig to about 60 psig; and/or a pressure drop across the continuous centrifuge, from inlet to outlet, of from about 3 to about 50 psig, from about 5 to about 40 psig, from about 10 to about 30 psig, or even from about 10 to about 20 psig; a solids concentration of the benefit agent delivery composition of from about 0.5 to 90% from about 1 to 50%, from about 5 to 40% and from about 10 to 35%; in one aspect, said centrifugal force in multiples of gravity may be from about 100 to about 20,000 from about 200 to about 10,000, from about 300 to about 9,000, from about 500 to about 8,000, from about 2,000 to about 7,000 multiples of gravity to said benefit agent delivery composition; and
c.) combinations thereof.

In one aspect of the aforementioned process said continuous process parameters may comprise:
a.) a centrifugal force in multiples of gravity of from about 100 to about 20,000 from about 200 to about 10,000, from about 300 to about 5,000, from about 500 to about 4,000, from about 1,000 to about 3,000 multiples of gravity to said benefit agent delivery composition; in another aspect, a centrifugal force may be in multiples of gravity of from about 100 to about 20,000 from about 200 to about 10,000, from about 300 to about 9,000, from about 500 to about 8,000, from about 2,000 to about 7,000 multiples of gravity to said benefit agent delivery composition
b.) an inlet fluid viscosity of from about 0.1 to about 2000 centipoise, from about 1 to 500 centipoise, from about 10 to 100 centipoise
c.) an inlet velocity of the benefit agent delivery composition of from about 0.2 to about 5 meters per second, from about 0.5 to about 5 meters per second, from about 1 to about 4 meters per second, or even from about 2 to about 3 meters per second;
d.) an the inlet pressure of the benefit agent delivery composition of from about 10 psig to about 120 psig, from about 20 psig to about 80 psig, from about 40 psig to about 60 psig;
e.) a pressure drop across the continuous centrifuge, from inlet to outlet, of from about 3 to about 50 psig, from about 5 to about 40 psig, from about 10 to about 30 psig, or even from about 10 to about 20 psig.

In one aspect of the aforementioned process, said process may comprise a filtration process selected from the group consisting of batch filtration, continuous filtration and combinations thereof, said process may comprise at least one of the following process parameters:
a.) a pressure differential across a filter media, said filter media having a median pore size is from about 10 kilo Dalton to about 30 microns, from about 300 kilo Dalton to about 20 microns, from about 0.15 microns to about 18 microns, from about 5 to about 15 microns;
b.) a pressure differential across a filter media of from about 5 psig to about 100 psig, from about 10 psig to about 80 psig, from about 20 psig to about 60 psig, or even from about 30 psig to about 50 psig;
c.) a permeate removal rate of from about 0.1 kg/min/ft$^2$ to about 50 kg/min/ft$^2$, from about 0.5 kg/min/ft$^2$ to about 30 kg/min/ft$^2$, from about 1.0 kg/min/ft$^2$ to about 20 kg/min/ft$^2$, from about 1.5 kg/min/ft$^2$ to about 10 kg/min/ft$^2$, or even from about 2 kg/min/ft$^2$ to about 5 kg/min/ft$^2$.

In one aspect of the aforementioned process, said process may comprise the following process parameters:
a.) a pressure differential across a filter media, said filter media having a median pore size is from about 10 kilo Dalton to about 30 microns, from about 300 kilo Dalton to about 20 microns, from about 0.15 microns to about 18 microns, from about 5 to about 15 microns;
b.) a pressure differential across a filter media of from about 5 psig to about 100 psig, from about 10 psig to about 80 psig, from about 20 psig to about 60 psig, or even from about 30 psig to about 50 psig; and
c.) a permeate removal rate of from about 0.1 kg/min/ft$^2$ to about 50 kg/min/ft$^2$, from about 0.5 kg/min/ft$^2$ to about 30 kg/min/ft$^2$, from about 1.0 kg/min/ft$^2$ to about 20 kg/min/ft$^2$, from about 1.5 kg/min/ft$^2$ to about 10 kg/min/ft$^2$, or even from about 2 kg/min/ft$^2$ to about 5 kg/min/ft$^2$.

In one aspect of the aforementioned process, said process may comprise drying said benefit agent delivery composition, said drying may comprise atomizing said benefit agent delivery composition to form benefit agent delivery composition droplets having a droplet size of from about 2 microns to about 200 microns, from about 10 microns to about 150 microns, from about 15 microns to about 100 microns, from about 20 microns to about 100 microns, from about 30 microns to about 80 microns, from about 50 microns to about 70 microns, said droplets being atomized in an atomization unit having at least one inlet and one outlet, at least one of said inlets having an inlet air temperature of from about 100° C. to about 280° C., from about 150° C. to about 230° C., from about 180° C. to 210° C., or even from about 190° C. to about 200° C., at least one of said outlets having an outlet air temperature of from about 50° C. to about 130° C., from about 70° C. to about 120° C., from about 90° C. to about 110° C., or even from about 95° C. to about 105° C.

In one aspect of the aforementioned process, said process may comprise, adsorption and/or absorption that may comprise contacting the benefit agent delivery composition with a adsorption and/or absorption media for from about 5 minutes to about 500 minutes, from about 10 minutes to about 400 minutes, from about 15 minutes to about 300 minutes, from about 20 minutes to about 200 minutes, from about 30 minutes to about 120 minutes, from about 30 minutes to about 60 minutes; at a benefit agent delivery composition temperature of from about 20° C. to about 110° C., from about 30° C. to about 90° C., from about 40° C. to about 80° C., from about 50° C. to about 80° C., from about 60° C. to about 80° C. and then separating said adsorption and/or absorption media and said benefit agent delivery.

In one aspect of the aforementioned process, said process may comprise flotation and/or decantation wherein the benefit agent delivery composition is permitted to separate into two or more benefit agent delivery composition components, one of said components comprising the majority of said shell particles and a second component comprising the majority of said encapsulated benefit agents said second component comprising said majority of said encapsulated benefit agent may be separated from the remainder of said benefit agent delivery components. In one aspect, the phase separation is accelerated by adjusting the density of the aqueous phase by the addition of salts (e.g. sodium chloride, magnesium chloride, calcium chloride, sodium sulfate, and the like). In one aspect, the phase separation is accelerated by increasing the temperature of the benefit agent delivery composition. In one aspect, the phase separation is accelerated by adding more of the aqueous phase, thus causing a dilution of the benefit agent delivery composition. In any one or combinations of these aspects of the invention, said benefit delivery composition is permitted to separate for a time of from about 0.5 hours to about 96 hours, from about 1 hour to about 72 hours, from about 3 hours to about 48 hours, from about 5 hours to about 24 hours, from about 8 hours to about 20 hours, from about 10 hours to about 16 hours, or even from about 12 hours to about 16 hours.

Applicants also disclose physical processes that may comprise the removal of a contaminant via desolvation processes, such processes generally comprising the steps of (1) addition of a miscible or immiscible solvent to the benefit agent delivery composition to maximize the concentration of the contaminant in the solvent phase, (2) removing the solvent phase containing the high concentration of contaminant, and (3) optionally, reconstituting the solvent-free cake of benefit agent delivery composition as a means to pass the benefit agent delivery composition through one or more additional processes, or alternatively, to improve the properties of the highly concentrated benefit agent delivery composition such that it is pumpable and handleable. Examples of processes that comprise these steps include, but are not limited to, centrifugation, filtration, solvent exchange, flash evaporation, decantation, flotation separation, spray drying, reactive adsorption, reactive absorption, electrophoretic separation and combinations thereof.

In one aspect, batch or continuous centrifugation is utilized to purify the benefit agent delivery composition. In a batch process, the benefit agent delivery composition is loaded into the centrifuge vessel, and sufficient gravitational force is applied to achieve a phase separation. The centrifugal force measurement that describes the centrifugal acceleration in multiples of gravity, is calculated by the following equation: $w^2 r/g$, the square of the angular velocity (in radians per second), multiplied by the distance from the center of the centrifuge to the end of the centrifuge tube (outer surface of the liquid layer, in centimeters), and dividing this by the gravitational force (981 centimeters per second, every second). The centrifugal force applied to the benefit agent delivery composition, in multiples of gravity, is from 100 to 20,000 from 200 to 10,000, from 300 to 5,000, from 500 to 4,000, from 1,000 to 3,000 multiples of gravity. In another aspect, the centrifugal force applied to the benefit agent delivery composition, in multiples of gravity, may be from 100 to 20,000 from 200 to 10,000, from 300 to 9,000, from 500 to 8,000, from 2,000 to 7,000 multiples of gravity. In a continuous process, the benefit agent delivery composition can be pumped into a device that imposes a centrifugal force to the benefit agent delivery composition. Such processes typically comprise a high inlet velocity and a high inlet pressure, and a circular motion of the fluid within the device to cause the movement of high density materials to the exterior wall, and lower density materials to the center. There are two exit points for the fluid from the device. In the case of a hydrocyclone, the lower density fluid in the center is removed from the device via a tube that extends into the center of the device, the flow rate of this stream is governed by the pressure drop at the exit of the stream. The higher density fluid is removed at the bottom of the device, the flow rate of this stream is governed by the pressure at the exit of the stream.

In the case of a disc stack centrifuge, the machine consists of a vertical, rotating bowl with an integral disc stack. The disc stack contains a set of truncated, conical discs separated by thin spacing or caulks. The feed is introduced to the rotating bowl in a non-disruptive manner through the inlet spindle, up to the bottom side of the disc stack. Guide ribs are then used to accelerate the slurry to the rotational speed of the bowl. Separation occurs in the narrow flow channel of the disc stack. The heavier solids are thrown outward by centrifugal force and once they reach the underside of the disc they slide down along the disc surface. Finally, the solids are thrown to the outermost position in the bowl where they begin collecting in the sediment holding space. The solids that are collected are continually removed under pressure through a bowl top outlet. The lighter clarified liquid moves to the center of the centrifuge and ultimately to the bowl top, where it is also discharged under pressure. The flow rate of both streams is governed by the pressure drop across the centrifuge. By manipulating the pressure drop across the higher density fluid, one can regulate the % solids and viscosity of the lower density fluid to achieve a continuous separation operation.

The inlet velocity of the benefit agent delivery composition (determined by dividing the volumetric flow rate of the benefit agent delivery composition by the cross-sectional area of the flow tube) can be 0.2 to 5 meters per second, from 0.5 to 5 meters per second, from 1 to 4 meters per second, or from 2 to 3 meters per second. The inlet pressure to the hydrocyclone or disc stack centrifuge can be 10 psig to 120 psig, from 20 psig to 80 psig, from 40 psig to 60 psig. The bottom of the hydrocyclone is exposed to atmospheric pressure, and this outlet collects the high density particulates and bulk phase. The outlet pressure at the top of the cyclone can be manipulated to achieve the right degree of separation of the high density bulk fluid and particulates from the desired benefit agent delivery particles. In a disc stack centrifuge, the low density fluid phase is collected at atmospheric pressure, whereas the pressure at the higher density fluid phase is manipulated to achieve the desired phase separation. Preferentially, there is at least a pressure difference between the inlet and outlet of the centrifuge, for example a hydrocyclone, of 3 to 50 psig, from 5 to 40 psig, from 10 to 30 psig, from 10 to 20 psig. Subsequent dilution of the concentrated benefit agent delivery composition can be applied before a second continuous centrifugation cycle. Multiple cycles result in improved purity of the benefit agent delivery composition. Optionally, the benefit agent delivery composition can be diluted with addition of processing materials after the final centrifugation cycle, in order to make the benefit agent delivery composition shippable, handleable. Such processing materials include, but are not limited to, benefit agent delivery composition dispersing and suspending agent. Such process equipment is available from Alfa-Lavel (Warminster, Pa., USA), Andritz Bird (Walpole, Mass., USA), Anhydro Inc. (Olympia Fields, Ill., USA), Contec Centrifuges (San Leandro, Calif., USA), Barrett Centrifugals (Worcester, Mass., USA), Ferrum (Houston, Tex., USA), KMPT USA Inc (Florence, Ky., USA).

In one aspect, the benefit agent delivery composition is purified via a filtration process. The benefit agent delivery composition, optionally diluted to adjust the flowability of the material, is loaded into a pressure filtration unit. The pressure filtration unit contains a membrane through which the benefit agent delivery composition is to be filtered. Such membrane can be a woven or nonwoven material. Wound polypropylene, polystyrene are examples of woven materials. Spunbound meltblown polypropylene, or polystyrene are examples of nonwoven materials. The membrane median pore size can vary from 10 kilo Dalton to 30 microns, from 300 kDa to 20 microns, from 0.15 microns to 18 microns, from 5 to 15 microns. The headspace of the pre-loaded benefit agent delivery composition is then pressurized with air to a pressure of 5 psig to 100 psig, from 10 psig to 80 psig, from 20 psig to 60 psig, from 30 psig to 50 psig. The rate of removal of the solvent phase from the benefit agent delivery composition is monitored. This rate is then divided by the filter area (total area through which the benefit agent delivery composition is filtered, i.e. the area over which the membrane is overlaid for filtration). The solvent phase is removed at a permeate rate of 0.1 kg/min/ft2 to 50 kg/min/ft2, from 0.5 to 30 kg/min/ft2, from 1.0 to 20 kg/min/ft2, from 1.5 to 10 kg/min/ft2, from 2 to 5 kg/min/ft2. Such process equipment is available from Precision Filtration Products (Pennsburg, Pa., USA), Vacudyne, Inc. (Chicago Heights, Ill., USA), Strainrite Companies (Auburn, Me., USA), Fil-Trek Corporation (Cambridge, Ontario, Canada), Oberlin Filter Co. (Waukesha, Wis., USA).

In one aspect, the benefit agent delivery composition is purified via a continuous filtration process. The benefit agent delivery composition is optionally diluted, and continuously pumped through a crossflow filtration cell. A portion of the solvent phase of the benefit agent delivery composition is removed through the membrane as permeate. The filtration cell comprises a microfiltration or ultrafiltration membrane. The membrane median pore size can vary from 10 kilo Dalton to 30 microns, from 300 kDa to 20 microns, from 0.15 microns to 18 microns, from 5 to 15 microns. The transmembrane pressure (the arithmetic average of the pressures before and after the membrane modulus minus the permeate pressure) is a function if the benefit agent delivery composition flowrate, and can be optimized by determining the pressure at which there is a maximum in the permeate flow rate. The transmembrane pressure can be from 5 psig to 150 psig, from 10 psig to 100 psig, from 20 psig to 80 psig, from 30 psig to 50 psig. The rate of removal of the solvent phase from the benefit agent delivery composition is monitored. This rate is then divided by the total filter area. The solvent phase is removed at a permeate rate of 0.1 kg/min/ft2 to 50 kg/min/ft2, from 0.5 to 30 kg/min/ft2, from 1.0 to 20 kg/min/ft2, from 1.5 to 10 kg/min/ft2, from 2 to 5 kg/min/ft2. Such process equipment is available from Pall Corporation (East Hills, N.Y., USA), GEA Filtration (Hudson, Wis., USA), and Millipore Corporation (Kankakee, Ill., USA).

In one aspect, the benefit agent delivery composition is purified via a spray drying process. The benefit agent delivery composition is optionally diluted to achieve the desired flowability of the material. The composition is then atomized through a centrifugal nozzle, a pressure nozzle, a two-fluid nozzle, or combinations thereof into a drying chamber. Airflow through the chamber is co-current or counter-current, preferably co-current at an inlet temperature of 100 degrees Centigrade to 280 degrees Centigrade, from 150 to 230 degrees Centigrade, from 180 to 210 degrees Centigrade, from 190 to 200 degrees Centigrade. The benefit agent delivery composition is atomized into a droplet size of 2 microns to 200 microns, from 10 microns to 150 microns, from 15 microns to 100 microns, from 20 microns to 100 microns, from 30 microns to 80 microns, from 50 microns to 70 microns. The dried particles are collected from the spray drying chamber through a cyclone, at an outlet air temperature of from 50 to 130 degrees Centigrade, from 70 to 120 degrees Centigrade, from 90 to 110 degrees centigrade, from 95 to 105 degrees Centigrade. Such process equipment is available from GEA Niro Inc. (Columbia, Md., USA), American Custom Drying (Burlington, N.J., USA), Spray-Tek Inc. (Middlesex, N.J., USA).

In one aspect, the benefit agent delivery composition is purified via a decantation process. The benefit agent delivery composition is placed in a vat, and allowed to age. Optionally, air is allowed to flow through the benefit agent delivery composition to increase the rate of phase separation. The benefit agent delivery composition is aged for 0.5 hours to 96 hours, from 1 hour to 72 hours, from 3 hours to 48 hours, from 5 hours to 24 hours, from 8 hours to 20 hours, from 10 hours to 16 hours, or even from 12 hours to 16 hours. The phase separated benefit agent delivery particles are skimmed off from the top of the benefit agent delivery composition in the vat. Such process equipment is available from Alfa-Laval Separation (Warminster, Pa., USA), Braodbent (Fort Worth, Tex., USA), Centrisys Corporation (Kenosha, Wis., USA), Contec Centrifuges (San Leandro, Calif., USA), Flottweg (Vilsbiburg, Germany), Decanter Machine (Johnson City, Tenn., USA), Jenkins Centrifuge (North Kansas City, Mo., USA), Pennwalt India (Searing Town, N.Y., USA).

In one aspect, the benefit delivery composition is purified via electrophoretic separation. The benefit delivery composition is optionally diluted and placed in a vessel with anode and cathode plates. In one aspect the anode is positioned near the lower end of the container. The cathode is positioned near the top. A potential is applied. The shell particles migrate to respective electrodes depending on polarity of the shell particles. With urea formaldehyde capsules particles were seen to migrate to the cathode.

The cathode is generally the electrode through which electric current flows out of a polarized electrical device, or where reduction occurs. Positively charged cation tend to move toward the cathode, and in the location where oxidation occurs. The anode tends to attract anions. Cationic changed particles tend to migrate to the cathode.

For electrophoretic separation, an electrical potential is applied between the electrodes such as with a dry cell or other voltage source.

For example a capsule slurry, at 10% solids can be placed in a beaker using a copper anode and cathode plate. A 6 volt charge is applied across the plates using a 6 volt lantern battery. The capsules are seen to migrate to the cathode in as little as twenty minutes.

In an alternate aspect, electrophoretic separation can be used alone or combined with any of the processes of centrifugation, filtration, solvent exchange, flash evaporation, decantation, flotation separation, spray drying, reactive absorption, reactive adsorption and combinations thereof.

The capsule slurry was ascertained to have a zeta potential more than 60, and therefore generally a stable emulsion. By applying an electric or magnetic field of sufficient potential, the colloidal particles can be made to coagulate or flocculate at one of the electrodes.

Electrophoretic separation can be applied in a batch or continuous process.

Encapsulates

Suitable encapsulates may be made by the teachings herein or purchased from Firmenich (Geneva, Switzerland), Givaudan (Argenteuil, France), IFF (Hazlet, N.J. USA), BASF (Ludwigshafen, Germany), Cognis (Monheim, Germany), Syngenta (Germany), Ciba (Basel, Switzerland), Rhodia Chimie (Lyon, France), Appleton Papers (Appleton, Wis., USA), Aveka (Minneapolis, Minn., USA), R.T. Dodge (Dayton, Ohio, USA). The wall materials of useful encapsulates may comprise materials selected from the group consisting of polyethylenes, polyamides, polystyrenes, polyisoprenes, polycarbonates, polyesters, polyacrylates, polyureas, polyurethanes, polyolefins, polysaccharides, epoxy resins, vinyl polymers, and mixtures thereof. In one aspect, useful wall materials include materials that are sufficiently impervious to the core material and the materials in the environment in which the encapsulated benefit agent will be employed, to permit the delivery benefit to be obtained. Suitable impervious wall materials include materials selected from the group consisting of reaction products of one or more amines with one or more aldehydes, such as urea cross-linked with formaldehyde or gluteraldehyde, melamine cross-linked with formaldehyde; gelatin-polyphosphate coacervates optionally cross-linked with gluteraldehyde; gelatin-gum Arabic coacervates; cross-linked silicone fluids; polyamine reacted with polyisocyanates and mixtures thereof. In one aspect, the wall material comprises melamine cross-linked with formaldehyde.

The core of the encapsulated benefit agent may comprise perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers and anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, and natural actives such as aloe vera, vitamin E, shea butter, cocoa butter, and the like, brighteners, antibacterial actives, antiperspirant actives, cationic polymers and mixtures thereof. In one aspect, said perfume raw material is selected from the group consisting of alcohols, ketones, aldehydes, esters, ethers, nitriles alkenes. In one aspect the core material may comprise a perfume. In one aspect, said perfume may comprise perfume raw materials selected from the group consisting of alcohols, ketones, aldehydes, esters, ethers, nitriles alkenes and mixtures thereof. In one aspect, said perfume may comprise a perfume raw material selected from the group consisting of perfume raw materials having a boiling point (B.P.) lower than about 250° C. and a ClogP lower than about 3, perfume raw materials having a B.P. of greater than about 250° C. and a ClogP of greater than about 3, perfume raw materials having a B.P. of greater than about 250° C. and a ClogP lower than about 3, perfume raw materials having a B.P. lower than about 250° C. and a ClogP greater than about 3 and mixtures thereof. Perfume raw materials having a boiling point B.P. lower than about 250° C. and a ClogP lower than about 3 are known as Quadrant I perfume raw materials, perfume raw materials having a B.P. of greater than about 250° C. and a ClogP of greater than about 3 are known as Quadrant IV perfume raw materials, perfume raw materials having a B.P. of greater than about 250° C. and a ClogP lower than about 3 are known as Quadrant II perfume raw materials, perfume raw materials having a B.P. lower than about 250° C. and a ClogP greater than about 3 are known as a Quadrant III perfume raw materials. In one aspect, said perfume comprises a perfume raw material having B.P. of lower than about 250° C. In one aspect, said perfume may comprise a perfume raw material selected from the group consisting of Quadrant I, II, III perfume raw materials and mixtures thereof. In one aspect, said perfume comprises a Quadrant III perfume raw material. Suitable Quadrant I, II, III and IV perfume raw materials are disclosed in U.S. Pat. No. 6,869,923 B1.

In one aspect, said perfume may comprise a Quadrant IV perfume raw material. While not being bound by theory, it is believed that such Quadrant IV perfume raw materials can improve perfume odor "balance". Said perfume may comprise, based on total perfume weight, less than about 30%, less than about 20%, or even less than about 15% of said Quadrant IV perfume raw material.

The perfume raw materials and accords may be obtained from one or more of the following companies Firmenich (Geneva, Switzerland), Givaudan (Argenteuil, France), IFF (Hazlet, N.J.), Quest (Mount Olive, N.J.), Bedoukian (Danbury, Conn.), Sigma Aldrich (St. Louis, Mo.), Millennium Specialty Chemicals (Olympia Fields, Ill.), Polarone International (Jersey City, N.J.), Fragrance Resources (Keyport, N.J.), and Aroma & Flavor Specialties (Danbury, Conn.).

Process of Making Encapsulated Benefit Agents

The encapsulated benefit agents employed herein may be made via the teachings of U.S. Pat. No. 6,592,990 B2 and/or U.S. Pat. No. 6,544,926 B1 and the examples disclosed herein.

Anionic emulsifiers are typically used during the encapsulation process to emulsify the benefit agent prior to microcapsule formation. While not being bound by theory, it is believed that the anionic materials adversely interact with the cationic surfactant actives that are often found in compositions such as fabric care compositions—this may yield an aesthetically unpleasing aggregation of particles that are employed in said composition. In addition to the unacceptable aesthetics, such aggregates may result in rapid phase separation of the particles from the bulk phase. Applicants discovered that such aggregates can be prevented by the addition of certain aggregate inhibiting materials including materials selected from the group consisting of salts, polymers and mixtures thereof. Useful aggregate inhibiting materials include, divalent salts such as magnesium salts, for example, magnesium chloride, magnesium acetate, magnesium phosphate, magnesium formate, magnesium bromide, magnesium titanate, magnesium sulfate heptahydrate; calcium salts, for example, calcium chloride, calcium formate, calcium calcium acetate, calcium bromide;

trivalent salts, such as aluminum salts, for example, aluminum sulfate, aluminum phosphate, aluminum chloride n-hydrate and polymers that have the ability to suspend anionic particles such as soil suspension polymers, for example, polyethylene imines, alkoxylated polyethylene imines, polyquaternium-6 and polyquaternium-7, xanthan gum, gellan gum, carageenan gum, carboxymethyl cellulose, and mixtures thereof.

In one aspect of the invention, encapsulated benefit agents are manufactured and are subsequently coated with a material to reduce the rate of leakage of the benefit agent from the particles when the particles are subjected to a bulk environment containing, for example, surfactants, polymers, and solvents. Non-limiting examples of coating materials that can serve as barrier materials include materials selected from the group consisting of polyvinyl pyrrolidone homopolymer, and its various copolymers with styrene, vinyl acetate, imidazole, primary and secondary amine containing monomers, methyl acrylate, polyvinyl acetal, maleic anhydride; polyvinyl alcohol homopolymer, and its various copolymers with vinyl acetate, 2-acrylamide-2-methylpropane sulfonate, primary and secondary amine containing monomers, imidazoles, methyl acrylate; polyacrylamides; polyacrylic acids; microcrystalline waxes; paraffin waxes; modified polysaccharides such as waxy maize or dent corn starch, octenyl succinated starches, derivatized starches such as hydroxyethylated or hydroxypropylated starches, carrageenan, guar gum, pectin, xanthan gum; modified celluloses such as hydrolyzed cellulose acetate, hydroxy propyl cellulose, methyl cellulose, and the like; modified proteins such as gelatin; hydrogenated and non-hydrogenated polyalkenes; fatty acids; hardened shells such as urea crosslinked with formaldehyde, gelatin-polyphosphate, melamine-formaldehyde, polyvinyl alcohol crosslinked with sodium tetraborate or gluteraldehyde; latexes of styrene-butadiene, ethyl cellulose, inorganic materials such as clays including magnesium silicates, aluminosilicates; sodium silicates, and the like; and mixtures thereof. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey U.S.A.

Suitable equipment for use in the processes disclosed herein may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., USA), Arde Barinco (New Jersey, USA).

Formaldehyde Scavenging

In one aspect, encapsulated benefit agent may be combined with a formaldehyde scavenger. In one aspect, encapsulated benefit agent may comprise the encapsulated benefit agent of the present invention. Suitable formaldehyde scavengers include materials selected from the group consisting of sodium bisulfate, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly (vinyl alcohol)-co-poly(vinyl amine), poly(4-aminostyrene), poly(l-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, or a mixture thereof. These formaldehyde scavengers may be obtained from Sigma/Aldrich/Fluka of St. Louis, Mo. U.S.A. or PolySciences, Inc. of Warrington, Pa. U.S.A.

In one aspect, resins that are insoluble in the benefit agent delivery composition are surface modified with such formaldehyde scavengers. Typically polymeric beads of 50 microns to 5000 microns, from 100 microns to 4500 microns, from 200 microns to 3500 microns, from 500 microns to 2000 microns, from 800 microns to 1500 microns are surface modified with formaldehyde scavenging materials. Such surface modified resins are incorporated into the benefit agent delivery composition and allowed to scavenge formaldehyde. Typically, the benefit agent delivery composition temperature is adjusted to 20 to 110 degrees Centigrade, from 30 to 90 degrees Centigrade, from 40 to 80 degrees Centigrade, from 50 to 80 degrees Centigrade, from 60 to 80 degrees Centigrade. Such formaldehyde scavengers are allowed to scavenge formaldehyde from the benefit agent delivery composition for 5 to 500 minutes, from 10 to 400 minutes, from 15 to 300 minutes, from 20 to 200 minutes, from 30 to 120 minutes, from 30 to 60 minutes. Subsequently, the insoluble resins are removed from the benefit agent delivery composition via a filtration process, to yield a polymer resin free benefit agent delivery composition. Examples of such resins include, but are not limited to, aminoethylated polystyrene, polymer bound diethylenetriamine, polymer bound p-toluenesulfonylhydrazine. Such materials are available from Aldrich (Milwaukee, Wis., USA). Commercial scavenging resins with tradenames ScavengePore®, Argopore®-NH2-L, JandaJel-NH2, Stratospheres PL-AMS are also available from Aldrich (Milwaukee, Wis., USA).

Such formaldehyde scavengers are typically combined with a slurry containing said benefit agent delivery particle, at a level, based on total slurry weight, of from about 2 wt. % to about 18 wt. %, from about 3.5 wt. % to about 14 wt. % or even from about 5 wt. % to about 13 wt. %.

In one aspect, such formaldehyde scavengers may be combined with a product containing a benefit agent delivery particle, said scavengers being combined with said product at a level, based on total product weight, of from about 0.005% to about 0.8%, alternatively from about 0.03% to about 0.5%, alternatively from about 0.065% to about 0.25% of the product formulation.

In another aspect, such formaldehyde scavengers may be combined with a slurry containing said encapsulated benefit agent, at a level, based on total slurry weight, of from about 2 wt. % to about 14 wt. %, from about 3.5 wt. % to about 14 wt. % or even from about 5 wt. % to about 14 wt. % and said slurry may be added to a product matrix to which addition an identical or different scavenger may be added at a level, based on total product weight, of from about 0.005% to about 0.5%, alternatively from about 0.01% to about 0.25%, alternatively from about 0.05% to about 0.15% of the product formulation, In one aspect, one or more of the aforementioned formaldehyde scavengers may be combined with a consumer product containing an encapsulated benefit agent at a level, based on total liquid fabric enhancing product weight, of from 0.005% to about 0.8%, alternatively from about 0.03% to about 0.4%, alternatively from about 0.06% to about 0.25% of the product formulation In one aspect, such formaldehyde scavengers may be combined with a liquid laundry detergent product containing a benefit agent delivery particle, said scavengers being selected from the group consisting of sodium bisulfite, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(l-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid and mixtures thereof, and combined with said liquid laundry detergent product at a level, based on total liquid laundry detergent product weight, of from about 0.003 wt. % to about 0.20 wt. %, from about 0.03 wt. % to about 0.20 wt. % or even from about 0.06 wt. % to about 0.14 wt. %.

In one aspect, such formaldehyde scavengers may be combined with a hair conditioning product containing a benefit agent delivery particle, at a level, based on total hair conditioning product weight, of from about 0.003 wt. % to about 0.30 wt. %, from about 0.03 wt. % to about 0.20 wt. % or even from about 0.06 wt. % to about 0.14 wt. %, said selection of scavengers being identical to the list of scavengers in the previous paragraph relating to a liquid laundry detergent product.

Compositions Comprising Benefit Agent Delivery Compositions

In one aspect, a consumer product comprising the benefit agent delivery composition as described in any of the various aspects of the product set forth herein and a consumer product adjunct is disclosed. In one aspect, said consumer product adjunct is selected from the group consisting of polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments and mixtures thereof.

In one aspect, said consumer product may comprise, based on total consumer product weight, from about 0.1% to about 20%, from about 0.2% to about 15%, from about 0.3% to about 10%, from about 0.4% to about 8%, or even from about 0.5% to about 5% of any of the benefit agent delivery compositions disclosed in the present specification.

In one aspect, a composition that may comprise any of the benefit agent delivery compositions of the present specification and a material selected from the group consisting of dyes; perfume; optical brighteners; deposition aids; and mixtures thereof.

In one aspect, a consumer product that may comprise, based on total consumer product weight:
  a.) from about 0.1% to about 5%, encapsulated benefit agent, said benefit agent comprising an amino resin;
    1. from about 1 ppm to about 150 ppm, from about 1 ppm to about 100 ppm, from about 1 ppm to about 50 ppm formaldehyde or even from about 1 ppm to about 10 ppm; and
    2. less than about 0.3 weight %, less than about 0.1 weight %, less than about 0.01 weight % from less than about 0.01 weight % to about 0.0001 weight % formaldehyde scavenger based on total consumer product weight is disclosed.

In one aspect, said consumer products may be a powdered, granule or other essentially dry detergent.

Aspects of the invention include the use of the benefit agent delivery composition of the present invention in laundry detergent compositions (e.g., TIDE™), hard surface cleaners (e.g., MR CLEAN™), automatic dishwashing liquids (e.g., CASCADE™), and floor cleaners (e.g., SWIFFER™). Non-limiting examples of cleaning compositions may include those described in U.S. Pat. Nos. 4,515,705; 4,537,706; 4,537,707; 4,550,862; 4,561,998; 4,597,898; 4,968,451; 5,565,145; 5,929,022; 6,294,514; and 6,376,445. The cleaning compositions disclosed herein are typically formulated such that, during use in aqueous cleaning operations, the wash water will have a pH of between about 6.5 and about 12, or between about 7.5 and 10.5. Liquid dishwashing product formulations typically have a pH between about 6.8 and about 9.0. Cleaning products are typically formulated to have a pH of from about 7 to about 12. Techniques for controlling pH at recommended usage levels include the use of buffers, alkalis, acids, etc., and are well known to those skilled in the art.

Method of Use

In one aspect, a method of treating and/or cleaning a situs, is disclosed. Said method may comprise optionally washing and/or rinsing said situs; contacting said situs with any single or combination of benefit agent delivery composition disclosed in the present specification; and optionally washing and/or rinsing said situs.

In one aspect, a situs treated in accordance with such method is disclosed.

Adjunct Materials

While not essential for the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' agglomerate/particle. The precise nature of these additional components, and levels of incorporation thereof, will depend on the physical form of the composition and the nature of the operation for which it is to be used. Suitable adjunct materials include, but are not limited to, polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' cleaning and fabric care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts is present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephos-phonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium.

Preferred MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Processes of Making and Using Compositions

The compositions of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

Method of Use

Compositions containing the encapsulated benefit agent disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a one or more of the benefit agent delivery compositions of the present invention or a consumer product comprising one or more of the benefit agent delivery compositions of the present invention and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

Test Methods

It is understood that the test methods that are disclosed in the Test Methods Section of the present application should be used to determine the respective values of the parameters of Applicants' invention as such invention is described and claimed herein.

(1) ClogP

The "calculated log P" (ClogP) is determined by the fragment approach of Hansch and Leo (cf., A. Leo, in Comprehensive Medicinal Chemistry, Vol. 4, C. Hansch, P. G. Sammens, J. B. Taylor, and C. A. Ramsden, Eds. P. 295, Pergamon Press, 1990, incorporated herein by reference). ClogP values may be calculated by using the "CLOGP" program available from Daylight Chemical Information Systems Inc. of Irvine, Calif. U.S.A.

(2) Boiling Point

Boiling point is measured by ASTM method D2887-04a, "Standard Test Method for Boiling Range Distribution of Petroleum Fractions by Gas Chromatography," ASTM International.

(3) Free Formaldehyde

Free formaldehyde is measured in accordance with NIOSH 5700 with the following adaptations:

Adaptation of DNPH concentration: minimize polymer degradation during derivatization reaction and create condition to monitor fate of derivatization reagent during subsequent LC analysis (check for potential reagent consumption by other sample constituents such as perfume carbonyls).

Reduction of the acid concentration and use of hydrochloric acid instead of perchloric acid: create milder conditions for derivatization, avoiding excessive polymer/resin degradation. (Derivatization kinetics at these conditions are checked to show reaction plateau is reached at about 10 min>>do we need to incorporate these reaction kinetics curves or not?).

Solvent extraction (Acetonitrile): ensures fast separation of the solid material from samples and allowing for easy filtration. The filtrate contains formaldehyde for analysis. Standard calibration solutions are made up to match the solvent composition to that of samples analyzed to ensure equal reaction conditions for derivatization.

Test Protocol & Apparatus

Apparatus

1) Waters HPLC instrumentation and Millennium system control and data acquisition system.
2) Continuous flow eluent vacuum degassing unit (Erma ERC-3612 or equivalent. Alternatively use He sparging)
3) Solvent delivery module (Waters 600E or equivalent multiple channel solvent delivery system)
4) Variable volume injector (Waters 717 plus, automatic injector or equivalent)
5) Analytical HPLC column/guard column (Symmetry C8, 3.9×1 50 mm, WAT no 054235 with guard column WAT no 054250 or equivalent)
6) UV detector (Waters 996 Photo Diode Array Detector or equivalent) 7) Data station (Waters Millennium 2010, 2020 C/S, or an equivalent system capable of storing and processing data).
8) Disposable filter units (0.45 μm, PTFE or 0.45 μm 25 mm, for sample filtration. Millipore Millex HV, cat. no. SLSR025NS)
9) Disposable syringes (Polypropylene 2 mL, with Luer fitting. Must match filtration unit female Luer.
10) Disposable glass sample vials, 4 mL, with caps. (Waters 4 mL clear glass vials with caps No. WAT025051, or equivalent)
11) Disposable filter cups, 0.45 μm, for eluent filtration. Millipore, cat no. SJHVM4710, or equivalent.
12) Lab Shaker+Lab Therm (Applitek Scientific Instruments or equivalent)
13) Titration equipment consisting of:
   a. Automatic titrator (Mettler DL70 or equivalent)
   b. Platinum electrode (Mettler DM140-Sc or equivalent)
   c. Titration vessel (100 mL, fitting DL70 or an equivalent automatic titrator system)

Reagents And Solutions

Reagents/Solvents (1) HPLC grade water (Resistivity above 18 free from organic material.
(2) Acetonitrile (HPLC Ultra Gradient Grade, J. T. Baker, no. 9017 or equivalent)
(3) Ion Pair Reagent: tetrabutylammonium hydrogen sulfate Pic reagent A Low UV, Waters no. WAT084189 or equivalent
(4) 2,4-dinitrophenylhydrazine ($C_6H_6N_4O_4$) Aldrich no 19,930-3 or equivalent
(5) Formaldehyde 37 wt. % in water, used as standard material. Aldrich, no 25,254-9 or equivalent (6) Ethanol absolute (J T Baker, no. 8006 or equivalent)
(7) Hydrochloric acid 36-38% (JT. Baker, no 6081 or equivalent)
(8) Iodine, volumetric standard, 0.1N solution in water Aldrich, no 31,898-1 or equivalent
(9) Sodium hydroxide, 1N (Aldrich, no 31,951-1 or equivalent)
(10) Hydrochloric acid, 1N (Aldrich, no 31,894-9 or equivalent)
(11) Sodium thiosulphate, volumetric standard, 0.1N solution in water Aldrich, no 31,954-6 or equivalent Solutions (1) Eluent A: water/ACN 90:10 with 5 mM Pic. Dissolve one bottle of Pic A Low UV into 900 mL of HPLC grade water. Add, while stirring vigorously, 100 mL of acetonitrile. Filter through a 0.45 μm disposable filter cup.
(2) Eluent B: water/ACN 30:70 with 5 mM Pic A. Dissolve one bottle of Pic A Low UV into 300 mL of HPLC grade water. Add very slowly, while stirring vigorously, 700 mL of acetonitrile. Filter through a 0.45 μm disposable filter cup. It is very important to mix well and add the acetonitrile very slowly to prevent the precipitation of the Pic A as much as possible. Preferably, prepare this eluent well in advance to allow equilibration and avoid precipitation during use. Filter before use.
(3) 2,4 Dinitrophenylhydrazine stock solution. Weigh, to the nearest 0.01 g, 0.4 g of 2,4-DNPH in a 100 mL glass bottle. Add 20 ml of ethanol absolute and stir vigorously. While stirring, add slowly 16 ml of concentrated hydrochloric acid, followed by 64 ml of ethanol absolute. The 2,4-DNPH stock solution can be kept for about 2 months.
(4) 2,4 Dinitrophenylhydrazine working solution for samples. Pipette 5 mL of the 2,4-dinitrophenylhydrazine stock solution into a 100 mL glass volumetric flask. Fill to volume with de ionized water and mix well. The 2,4-DNPH working solution has to be re-made daily.
(5) 2,4 Dinitrophenylhydrazine working solution for standards. Pipette 5 mL of the 2,4-dinitophenylhydrazine stock solution into a 100 mL glass volumetric flask. Fill to volume with acetonitrile mix well. The 2,4-DNPH working solution has to be re-made daily.

Procedure

1) Formaldehyde standard stock solution: Weigh, to the nearest 0.0001 gram, 1.0 g of formaldehyde standard into a small sample cup. Dissolve into a 1 L volumetric flask using deionized water. Record the weight as Wst
2) Preparation of standard working solutions
   a. Pipette 5 mL of the formaldehyde stock solution into a 50 mL volumetric flask. Bring to volume with de ionized water and mix well.
   b. Pipette 0, 0.5, 1.0, 3, and 5 mL of the diluted stock solution into separate 50 mL volumetric flasks. Bring to volume with de ionized water and mix well. Filter approximately 5 mL of each standard working solution through a 0.45 μm disposable filter unit into a glass vial.
3) Sample preparation: Weigh, to the nearest 0.0001 gram, about 1 gram of sample into a 50 mL volumetric flask. Bring to volume with acetonitrile and mix well. Allow about five (5) minutes for the insoluble material to settle. Filter approximately 5 mL of the sample solution through a 0.45 μm disposable filter unit into a glass vial. Record the exact weight as Wsa in grams.

4) Derivatization procedure
   a. Pipette 1.00 mL of each standard solution, filtered sample solution, and filtered extract into separate 4 mL sample vials. The choice of the calibration range is dependent on the expected free formaldehyde level in sample solutions or extracts.
   b. Standards: add 1.00 mL of 2,4-DNPH working solution for standards to each vial. Stopper and mix.
   c. Samples: add 1.00 mL of 2,4-DNPH working solution for samples to each vial. Stopper and mix.
   d. Let react for 10 minutes±20 seconds before injection. Note: this timing is critical. Start the timer as soon as the reagents are mixed and take into account the time it takes to load and inject a sample.
5) Instrumental Operation: Set up the HPLC system according to the manufacturer's instructions using the following conditions:
   Isocratic: 20% A-80% B/0.8 ml/min
   Detection: UV at 365 nm
   Inj. volume: 20 μl
   Runtime: 10 minutes Calibration 1) Inject 20 μl of a derivatized standard solution at least once to check for proper instrument functioning (Never use the area counts of the first injection for calibration purposes. The first injection after start up of the HPLC system is generally not representative).
2) Inject 20 μl of each of the derivatized standard solutions.
3) Record the peak areas and, with the help of the examples in appendix 9, assign the peak identity.

Analysis of the Samples

1) Inject 20 μl of each of the derivatized sample solutions or extracts.
2) Record the peak area for the formaldehyde peak.
3) After analyses are finished, replace the eluent by de ionized water and then a storage solvent, e.g. HPLC grade methanol, before removing the column from the system.

Calculations (1) Calculate the amount of formaldehyde in each of the standard solutions (calibration range: 0-5 μg/mL)

$$\underline{\text{vol}} \; \mu g \; \text{formaldehyde/mL} = \frac{Wst \times Ast \times 1000 \times Dil \; \text{vol}}{100 \times 10 \times 50} = \frac{Wst \times Ast \times Dil}{50}$$

Where:
   Wst=weight of standard in the stock solution in grams (7.1.1)
   Ast=Activity of the standard material (%) determined by titration (7.1.5)
   Dil vol=diluted standard stock amounts in mL used for preparing standard solutions (0-10 mL)
(2) Construct a calibration curve (amounts versus peak area). When using the Waters Millennium 2010 data processing software, perform the 'Fit Type': Linear calibration setting in 'Component table' of the Processing Method.
(3) Starting from the formaldehyde peak area of a sample, read the amount of formaldehyde in the sample solution or extract in μg/mL from the calibration curve. Record this value as $\mu g_{sa}$ Note: this calculation assumes that injection volumes of standards and samples are identical.

(4) Calculate the amount of formaldehyde in the samples as follows:

$$\text{ppm formaldehyde} = \frac{\mu gsa \times 100}{Wsa}$$

Where: μgsa=amount of free formaldehyde in the sample solution in μg/mL (7.3)
Wsa=weight of sample in grams (7.3.1)

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

80 wt % Core/20 wt % Wall Melamine Formaldehyde (MF) Capsule 18 grams of a blend of 50% butyl acrylate-acrylic acid copolymer emulsifier (Colloid C351, 25% solids, pka 4.5-4.7, Kemira) and 50% polyacrylic acid (35% solids, pKa 1.5-2.5, Aldrich) is dissolved and mixed in 200 grams deionized water. The pH of the solution is adjusted to pH of 3.5 with sodium hydroxide solution. 6.5 grams of partially methylated methylol melamine resin (Cymel 385, 80% solids Cytec) is added to the emulsifier solution. 200 grams of perfume oil is added to the previous mixture under mechanical agitation and the temperature is raised to 60° C. After mixing at higher speed until a stable emulsion is obtained, the second solution and 3.5 grams of sodium sulfate salt are poured into the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.6, 30 grams of partially methylated methylol melamine resin (Cymel 385, 80% Cytec). This mixture is heated to 75° C. and maintained 6 hours with continuous stirring to complete the encapsulation process. An average capsule size of 20 um is obtained as analyzed by a Model 780 Accusizer. The measured free formaldehyde concentration in the perfume microcapsule slurry is 5000 ppm.

Example 2

84 wt % Core/16 wt % Wall Melamine Formaldehyde (MF) Capsule 25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, N.J., U.S.A.)) is added to the emulsifier solution. 200 grams of perfume oil is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. An average capsule size of 20 um is obtained as analyzed by a Model 780 Accusizer. The measured free formaldehyde concentration in the perfume microcapsule slurry is 3500 ppm.

Example 3: Spray Drying

The perfume microcapsule slurry of Example 1 is pumped at a rate of 1 kg/hr into a co-current spray dryer (Niro Production Minor, 1.2 meter diameter) and atomized using a centrifugal wheel (100 mm diameter) rotating at 18,000 RPM. Dryer operating conditions are: air flow of 80 kg/hr, an inlet air temperature of 200 degrees Centigrade, an outlet temperature of 100 degrees Centigrade, dryer operating at a pressure of −150 millimeters of water vacuum. The dried powder is collected at the bottom of a cyclone. The collected particles have an approximate particle diameter of 20 microns. The measured free formaldehyde is 5000 milligrams per liter. The equipment used the spray drying process may be obtained from the following suppliers: IKA Werke GmbH & Co. KG, Janke and Kunkel—Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Example 4: Solvent Exchange 150 grams of propylene glycol is added to 100 grams of the perfume microcapsules of Example 1. The mixture is prepared at 25 C, and placed in a rotary flash evaporator (Buchi Rotavapor R-114). A water bath (Baxter Scientific Products Durabath) is used to heat and maintain the mixture at 65 C for 6 hours, with an initial vacuum of 15 inches of mercury that is raised to 28.2 inches of mercury over the duration of the evaporation (Welch 1400 DuoSeal vacuum pump). The rate of vacuum increase is governed by the amount of water in the mixture and minimizing the risk of "popping" over the mixture. The final water content is measured to be 1.1 wt %, solids content of 21%, and the free formaldehyde in the slurry is 2990 milligrams per liter.

200 grams of glycerol is added to 100 grams of the perfume microcapsules of Example 1. The mixture is prepared at 25 C, and placed in a rotary flash evaporator (Buchi Rotavapor R-114). A water bath (Baxter Scientific Products Durabath) is used to heat and maintain the mixture at 65 C for 8 hours, with an initial vacuum of 15 inches of mercury that is raised to 28.2 inches of mercury over the duration of the evaporation (Welch 1400 DuoSeal vacuum pump). The rate of vacuum increase is governed by the amount of water in the mixture and minimizing the risk of "popping" over the mixture. The final water content is 2 wt %, solids content is 17 wt %, and the free formaldehyde in the slurry is 2550 milligrams per liter.

Example 5: Batch Filtration

Example 5B is prepared by mixing 50 grams of the perfume microcapsule slurry of Example 1 (pH 5.0) with 60 grams of deionized water. The mixture is heated to 65 degrees Centigrade. The mixture is then poured onto a batch filter assembly. The batch filter assembly comprises a Buchner funnel with a 250 micron sieve, onto which is laid a membrane (WPP807—wound polypropylene, 15 micron pore size; or 2.0 SM—spunbound meltblown nonwoven, 17 micron pore size), filtration area of 0.011 square feet. The entire assembly can be pressurized up to 40 psig pressure. The permeate passes through the membrane, then through the large pore sieve, and is collected. After adding the perfume microcapsule mixture onto the membrane, the entire assembly is pressurized to 40 psig. The rate of permeate collection is monitored. The assembly is depressurized after 3 minutes, and the dewatered perfume microcapsule cake is removed.

| Example ID | Membrane | Mass of Example 1 Slurry (g) | Mass of Water Added (g) | Free CH$_2$O in Cake | Free CH$_2$O in Permeate | Total CH$_2$O in Slurry |
|---|---|---|---|---|---|---|
| 5A | WPP807 | 50 | 0 | 2593 | 7118 | 4403 |
| 5B | WPP807 | 50 | 30 | 1407 | 4093 | 4264 |
| 5E | 2.0SM | 50 | 0 | 1983 | 7006 | 3992 |
| 5F | 2.0SM | 50 | 30 | 1407 | 3807 | 4153 |

Example 6: Batch Filtration

The 2.0SM membrane of Example 5 shows the best results for minimizing free formaldehyde in the filtered cake. This membrane is utilized to determine the effect of pre-dilution and pH adjustment (with 50 wt % citric acid) of the perfume microcapsules of Example 1.

| Example ID | Mass of deionized water added to 50 grams of perfume microcapsules of Example 1 (pH 5.0) | Free Formaldehyde in a PMC Cake |
|---|---|---|
| 6A | 0 | 3259 |
| 6B | 30 | 2416 |
| 6C | 60 | 1917 |
| 6D | 90 | 1906 |
| 6E | 120 | 1779 |
| 6F | 150 | 1527 |

| Example ID | Description | Free Formaldehyde (milligrams per liter) |
|---|---|---|
| 6G | Example 1, pH 2.5 Cake | 1047 |
| 6H | Example 1, pH 2.0 Cake | 1061 |
| 6I | Example 1, pH 1.5 Cake | 1236 |

The expected free formaldehyde in the samples above is 1000 milligrams per liter (based on the quantity of formaldehyde in the sample initially, and removal of water during the filtration process). The filtered cakes 6G, 6H, and 6I are reconstituted in an aqueous slurry to yield a phase stable suspension in the following way: to 20.8 grams of the filtered cake is added 10.6 grams of DI water, then 6.0 grams of 1 wt % aqueous solution of Optixan Xanthan Gum (ADM Corporation), and 2.50 grams of 32 wt % magnesium chloride solution. The aqueous suspensions are aged 1 week at 25° C., prior to measuring the free formaldehyde.

| Example ID | Description | Free Formaldehyde (milligrams per liter) | Expected Free Formaldehyde (milligrams per liter) |
|---|---|---|---|
| 6J | Cake 6G, reconstituted | 1329 | 480 |
| 6K | Cake 6H, reconstituted | 1524 | 480 |
| 6L | Cake 6I, reconstituted | 1857 | 480 |

There is a "reservoir" of formaldehyde that generates free formaldehyde in the bulk solution. This "reservoir" cannot be eliminated by dilution+filtering, nor reducing the pH of the slurry prior to filtration.

Example 7: Continuous Filtration

Continuous diafiltration of the PMC slurry is completed through two different sized membranes—0.14 micron (Zirconium Dioxide+Titanium Dioxide, from TAMI Industries of France), and 300 kilo Dalton (Zirconium Dioxide, from TAMI Industries of France). 3 parts water is added to 1 part of perfume microcapsules of Example 1 (but with free formaldehyde in the bulk adjusted to 1200 ppm using acetoacetamide as a scavenger). This slurry is then used to determine the ideal flowrate through the x-membrane filter by running the continuous filtration operation at 4 different flow rates, and measuring the permeate collection rate, and the pressure drop across the membrane. The optimum transmembrane pressure drop and flowrate that maximize permeate collection rate is found to be 300 Liters per hour and 4 bar for the 300 kDa membrane, and 230 Liters per hour and 5 bar for the 0.14 micron membrane. Then, the slurry is filtered across each membrane 5 times (in order to remove all of the water that had been added to the slurry). This constitutes 1 pass. The material is then again diluted with 3 parts water for every 1 part diafiltered slurry. The slurry is then filtered across the membrane to remove the added water. This constitutes 2 passes. A total of 5 passes through the diafilter membrane are completed with each of the membranes.

| Example ID | Description | Free Formaldehyde (ppm) |
|---|---|---|
| 7A | 3:1 water:PMC slurry dilution, no diafiltration | 316.5 |
| 7B | 1 pass diafiltration, 0.14 micron membrane | 300.4 |
| 7C | 2 pass diafiltration, 0.14 micron membrane | 332.3 |
| 7D | 3 pass diafiltration, 0.14 micron membrane | 250.1 |
| 7E | 4 pass diafiltration, 0.14 micron membrane | 196.5 |
| 7F | 5 pass diafiltration, 0.14 micron membrane | 106.7 |
| 7G | 1 pass diafiltration, 300 kDa membrane | N/A |
| 7H | 2 pass diafiltration, 300 kDa membrane | 355.3 |
| 7I | 3 pass diafiltration, 300 kDa membrane | 243.6 |

-continued

| Example ID | Description | Free Formaldehyde (ppm) |
|---|---|---|
| 7J | 4 pass diafiltration, 300 kDa membrane | 183.9 |
| 7K | 5 pass diafiltration, 300 kDa membrane | 148.2 |

Note that there is not a significant reduction in free formaldehyde (there is a "reservoir" of formaldehyde).

Example 8: Batch Centrifuge 14 milliliters of the aqueous suspension of perfume microcapsules of Example 1 are placed in a 20 milliliter centrifuge tube. 6 identical tubes are prepared and placed in a batch centrifuge (IEC Centra CL2). After 20 minutes at 3800 RPM, the centrifuge tubes are removed, and three layers are observed: perfume microcapsule cake layer on top, followed by an aqueous layer, followed by a high density solid particulate layer. The top microcapsule layer is isolated from the remaining material, and submitted for free formaldehyde analysis. The microcapsule cake is also reconstituted to make a phase stable suspension (To 20.8 grams of the top perfume microcapsule layer is added 10.6 grams of DI water, then 6.0 grams of 1 wt % aqueous solution of Optixan Xanthan Gum from ADM Corporation, and 2.50 grams of 32 wt % magnesium chloride solution from Chemical Ventures). Free formaldehyde in PMC layer (top layer) is measured to be 2244 milligrams per liter. Free Formaldehyde in the reconstituted microcapsules (2 wk/25 C aged) is measured to be 1083 milligrams per liter. The free formaldehyde shows the expected trend, a decrease in level that is proportional to the amount of dilution water that is added. i.e. the "reservoir" of formaldehyde has been removed by this physical separation technique.

Example 9: Batch Centrifuge

The perfume microcapsules slurry of Example 2 is pH adjusted with 50 wt % citric acid. 14 milliliters of the aqueous suspension of perfume microcapsules of Example 2 are placed in a 20 milliliter centrifuge tube. 6 identical such tubes are prepared and placed in a batch centrifuge (IEC Centra CL2). After 20 minutes at 3800 RPM, the centrifuge tubes are removed, and three layers are observed: perfume microcapsule cake layer on top, followed by an aqueous layer, followed by a high density solid particulate layer. The top microcapsule layer is isolated from the remaining material. To 20.8 grams of the top perfume microcapsule layer is added 10.6 grams of DI water, then 6.0 grams of 1 wt % aqueous solution of Optixan Xanthan Gum from ADM Corporation, and 2.50 grams of 32 wt % magnesium chloride solution from Chemical Ventures. The top microcapsule layer, and the reconstituted perfume microcapsule slurry are analyzed for free formaldehyde content (Example 9A, 9B).

| Example ID | Description | Free CH2O (cake) | Free CH2O (reconstituted) |
|---|---|---|---|
| 8A, 8B | Example 2 (pH 5.3) Batch Centrifuge (CONTROL) | 2244 | 1083 |
| 9A, 9B | Example 2, pH 2.5, Batch Centrifuge | 2151 | 1141 |

Example 10: Batch Centrifuge 14 milliliters of the aqueous suspension of perfume microcapsules of Example 2 are placed in a 20 milliliter centrifuge tube. 6 identical such tubes are prepared and placed in a batch centrifuge (IEC Centra CL2). After 20 minutes at 3800 RPM, the centrifuge tubes are removed, and three layers are observed: perfume microcapsule cake layer on top, followed by an aqueous layer, followed by a high density solid particulate layer. The top microcapsule layer is isolated from the remaining material. 4 grams of the top microcapsule layer is mixed with 8 grams of deionized water. 4 identical such tubes are prepared and batch centrifuged. The top microcapsule layer from the centrifuged tubes is removed and free formaldehyde is analyzed (Example 10A, 2 passes).

4 grams of the top microcapsule layer of Example 8E is mixed with 8 grams of deionized water. 2 identical such tubes are prepared and batch centrifuged (IEC Centra CL2, 20 minutes at 3800 RPM, 25 C). The top microcapsule layer from the centrifuge tubes is isolated and analyzed for free formaldehyde (Example 10B, 3 passes). The analysis shows that one can permanently remove free formaldehyde from the perfume microcapsules by increasing the number of centrifuge cycles.

| Example ID | Description | Free CH$_2$O (cake) | Free CH$_2$O (reconstituted) |
|---|---|---|---|
| 8A, 8B | Example 2 (pH 5.3) - 1 pass Batch Centrifuge | 2244 | 1083 |
| 10A | Example 2 (pH 5.3) - 2 passes Batch Centrifuge | 581 | N/A |
| 10B | Example 2 (pH 5.3) - 3 passes Batch Centrifuge | 326 | N/A |

The perfume microcapsule cakes 8A, 10A, and 10B are reconstituted in water (To 20.8 grams of the top perfume microcapsule layer is added 10.6 grams of DI water, then 6.0 grams of 1 wt % aqueous solution of Optixan Xanthan Gum from ADM Corporation, and 2.50 grams of 32 wt % magnesium chloride solution from Chemical Ventures), and aged for 96 hours at 35 degrees Centigrade.

| Example ID | Description | Free CH$_2$O (cake) | Free CH$_2$O (reconstituted, aged 96 hr/35° C.) |
|---|---|---|---|
| 8A, 10C | Example 2 (pH 5.3) - 1 pass Batch Centrifuge | 2244 | 1466 |
| 10A, 10D | Example 2 (pH 5.3) - 2 passes Batch Centrifuge | 581 | 594 |
| 10B, 10E | Example 2 (pH 5.3) - 3 passes Batch Centrifuge | 326 | 411 |

There is a rise in free formaldehyde from 1083 ppm to 1466 ppm for the once centrifuged slurry. Multiple centrifuge cycles are efficient in reducing the rise of free formaldehyde upon ageing.

The pH adjustment of perfume microcapsules of Example 2 yields a significant rise in releasable formaldehyde (3116 ppm to 6100 ppm). The centrifuged perfume microcapsules yield a much lesser rise in releasable formaldehyde, indicating that a large reservoir of free formaldehyde has been removed during the centrifugation process.

| Example ID | Description | Free CH$_2$O Reconstituted Slurry pH 4.3 | Free CH$_2$O Reconstituted Slurry pH adjusted 2.5 1 wk/25° C. ageing |
|---|---|---|---|
| 8B, 10F | Example 2 (pH 5.3) - 1 pass Batch Centrifuge | 1083 | 1216 |
| 10G, 10H | Example 2 (pH 5.3) - no centrifuge | 3116 | 6100 |

Example 11: Reactive Adsorption

Approximately 1.0 grams of the perfume microcapsules of Example 1 are placed into a glass jar. Approximately 1.0 grams of deionized water is added to the jar. Polymeric resin is then added to the diluted perfume microcapsule slurry. The sample is speed mixed at 3000 RPM for 2 minutes and allowed to sit overnight at 25 degrees Centigrade. The sample is speed mixed the next morning at 3000 RPM for 2 minutes. The slurry is filtered to remove the polymeric resin, and free formaldehyde is measured. A description of the experiments is summarized in the table below. The free formaldehyde of the perfume microcapsule slurry prior to any addition of polymeric resins is measured to be 4800 ppm.

| Resin/Scavenger | Mass of slurry (g) | Mass of water (g) | Measured Free Formaldehyde |
|---|---|---|---|
| ScavengePore ®-aminomethylated polystyrene | 1.1175 | 1.0000 | 63.0 |
| Poly (4-vinylpyridine) | 1.0218 | 1.0000 | 5060.8 |
| Diethylenetriamine, polymer-bound | 1.0614 | 1.0000 | 3477.1 |
| p-Toluenesulfonylhydrazide, polymer-bound | 1.0608 | 1.0000 | 183.5 |
| 10% PVOH/PVAm M12 solution | 1.0452 | 0.0000 | 3611.4 |
| ScavengePore ®-aminomethylated polystyrene | 2.0137 | 2.0175 | 76.9 |
| ScavengePore ®-aminomethylated polystyrene | 2.0821 | 1.0936 | 67.1 |
| p-Toluenesulfonylhydrazide, polymer-bound | 2.0017 | 2.0399 | 59.8 |
| p-Toluenesulfonylhydrazide, polymer-bound | 2.0099 | 0.0000 | 142.1 |
| ArgoPore ®-NH$_2$ HL | 2.0059 | 1.0023 | 3.6 |
| JandaJel-NH$_2$ | 2.0319 | 1.0020 | 505.0 |
| StratoSpheres PL-AMS | 2.0042 | 1.0021 | 831.8 |
| StratoSpheres PL-AMS | 2.1262 | 1.0022 | 654.4 |
| Aminomethyl polymer resin | 2.0041 | 1.0021 | 551.0 |
| ArgoPore ®-NH2 HL | 2.0059 | 1.0023 | 146.9 |

Example 12: Finished Product Compositions

Non-limiting examples of product formulations containing purified perfume microcapsules of the aforementioned examples are summarized in the following table.

| | EXAMPLES (% wt) | | | | | | | | | |
|---|---|---|---|---|---|---|---|---|---|---|
| | A | B | C | D | E | F | G | H | I | J |
| FSA$^a$ | 14 | 16.47 | 14 | 12 | 12 | 16.47 | — | — | 5 | 5 |
| FSA$^b$ | — | — | — | — | — | — | 3.00 | — | — | — |
| FSA$^c$ | — | — | — | — | — | — | — | 6.5 | — | — |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch$^d$ | 1.25 | 1.47 | 2.00 | 1.25 | — | 2.30 | 0.5 | 0.70 | 0.71 | 0.42 |
| Microcapsule (% active)* | 0.6 | 0.75 | 0.6 | 0.75 | 0.37 | 0.60 | 0.37 | 0.6 | 0.37 | 0.37 |
| Phase Stabilizing Polymer$^f$ | 0.21 | 0.25 | 0.21 | 0.21 | 0.14 | — | — | 0.14 | — | — |
| Suds Suppressor$^g$ | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA$^h$ | 0.017 | 0.017 | 0.017 | 0.017 | 0.007 | 0.007 | 0.20 | — | 0.002 | 0.002 |
| Preservative (ppm)$^{i,j}$ | 5 | 5 | 5 | 5 | 5 | 5 | — | 250$^j$ | 5 | 5 |
| Antifoam$^k$ | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant$^l$ | 0.01 | 0.01 | 0.01 | 0.01 | 0.01 | 0.01 | 0.01 | 0.01 | 0.01 | 0.01 |

-continued

| | EXAMPLES (% wt) | | | | | | | | | |
|---|---|---|---|---|---|---|---|---|---|---|
| | A | B | C | D | E | F | G | H | I | J |
| Neat Unencapsulated Perfume | 0.8 | 0.7 | 0.9 | 0.5 | 1.2 | 0.5 | 1.1 | 0.6 | 1.0 | 0.9 |
| Deionized Water | Balance | Balance | Balance | Balance | Balance | Balance | Balance | Balance | Balance | Balance |

[a] N,N-di(tallowoyloxyethyl)-N,N-dimethylammonium chloride.
[b] Methyl bis(tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[f] Copolymer of ethylene oxide and terephthalate having the formula described in U.S. Pat. No. 5,574,179 at col.15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
[l] Hydrophobically-modified ethoxylated urethane available from Rohm and Haas under the tradename Aculyn™ 44.
*Suitable combinations of the microcapsules provided in Examples 1 through 7. (Percent active relates to the core content of the microcapsule.)

The formaldehyde levels of the compositions of Example 12 are measured in accordance with Test Method 3 of the present specification are found to have formaldehyde levels of less than 50 ppm.

Example 13: Microcapsules in Dry Laundry Formulations

Non-limiting examples of product formulations containing purified perfume microcapsules of the aforementioned examples are summarized in the following table.

| Component | % w/w granular laundry detergent composition | | | | | | |
|---|---|---|---|---|---|---|---|
| | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |

-continued

|  | % w/w granular laundry detergent composition Component | | | | | | |
|---|---|---|---|---|---|---|---|
|  | A | B | C | D | E | F | G |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |
| Perfume microcapsules* | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

*Microcapsule added as 35% active slurry (aqueous solution). Core/wall ratio can range from 80/20 up to 90/10 and average particle diameter can range from 5 μm to 50 μm, and can be purified via any of the aforementioned examples.

The formaldehyde levels of the compositions of Example 13 are measured in accordance with Test Method 3 of the present specification are found to have formaldehyde levels of less than 10 ppm.

Example 14: Liquid Laundry Formulations (HDLs)

Non-limiting examples of product formulations containing purified perfume microcapsules of the aforementioned examples are summarized in the following table.

The formaldehyde levels of the compositions of Example 14 are measured in accordance with Test Method 3 of the present specification are found to have formaldehyde levels of less than 10 ppm.

Example 15

Non-limiting examples of product formulations containing purified perfume microcapsules of the aforementioned examples are summarized in the following table.

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Perfume Microcapsules* | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

Microcapsule added as 35% active slurry (aqueous solution). Core/wall ratio can range from 80/20 up to 90/10 and average particle diameter can range from 5 μm to 50 μm, and can be purified via any of the aforementioned examples.

| Examples of liquid detergents | A | B | C | D |
|---|---|---|---|---|
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | 0.40 |
| C12-C14 alkyl poly ethoxylate (3) sulfate Na salt | 10.60 | 6.78 | 10.60 | 10.60 |
| Linear Alkylbenzene sulfonate acid | 0.19 | 1.16 | 0.79 | 0.79 |
| Citric Acid | 3.75 | 2.40 | 3.75 | 3.75 |
| C12-C18 Fatty Acid | 4.00 | 2.56 | 7.02 | 7.02 |
| Enzymes | 0.60 | 0.4 | 0.60 | 0.60 |
| Boric Acid | 2.4 | 1.5 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.09 | 0.06 | 0.14 | 0.14 |
| Hydrogenated Castor Oil | 0.05 | 0.300 | 0.20 | 0.20 |
| Ethanol | 2.50 | 1.00 | 2.50 | 2.50 |
| 1,2 propanediol | 1.14 | 0.7 | 1.14 | 1.14 |
| Sodium hydroxide | 3.8 | 2.6 | 4.60 | 4.60 |
| Mono Ethanol Amine | 0.8 | 0.5 | | |
| Na Cumene Sulphonate | | | | |
| Silicone emulsion | 0.0030 | 0.0030 | 0.0030 | 0.0030 |
| Dye | 0.002 | 0.002 | 0.002 | 0.002 |
| Opacifier (Styrene Acrylate based) | | | | |
| Bentonite Softening Clay | | | | |
| Acrylamide/MAPTAC (ex Nalco Chemicals of Naperville, IL) | | | 0.40 | 0.40 |
| Mirapol 550 (ex Rhodia Chemie, France) | | | | |
| Polyquaternium 10 - Cationic hydroxyl ethyl cellulose | | | | |
| PP-5495 (silicone ex Dow Corning Corporation, Midland, MI) | | | | |
| DC 1664 (silicone ex Dow Corning Corporation, Midland, MI) | | | | |
| Pearlescent agent* | | | | 0.2 |
| Perfume micro capsules** (expressed as perfume oil) | 0.8 | 0.5 | 1.0 | 0.7 |
| Perfume | 0.7 | 0.55 | 1.00 | 1.00 |
| Poly Ethylene Imine MW 25000 | | | | |
| Water | Up to 100 | Up to 100 | Up to 100 | Up to 100 |

*Mica-TiO$_2$ (Prestige Silk Silver Star ex Eckart) or BiOCl (Biron Silver CO-Merck) or pre-crystallized EGDS (Tegopearl N 100 ex Degussa, expressed as pure EGDS)
**Microcapsule added as 35% active slurry (aqueous solution). Core/wall ratio can range from 80/20 up to 90/10 and average particle diameter can range from 5 μm to 50 μm, and can be purified via any of the aforementioned examples.

| Examples of liquid detergents | E | F | G | H |
|---|---|---|---|---|
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | |
| C12-C14 alkyl poly ethoxylate (3) sulfate Na salt | 10.60 | 6.78 | 10.60 | 10.60 |
| Linear Alkylbenzene sulfonate acid | 0.79 | 1.19 | 0.79 | 0.79 |
| Citric Acid | 3.75 | 2.40 | 3.75 | 3.75 |
| C12-C18 Fatty Acid | 7.02 | 4.48 | 7.02 | 7.02 |
| Enzymes | 0.60 | 1.0 | 0.60 | |
| Boric Acid | 1.25 | 1.25 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.14 | 0.06 | 0.14 | |
| Hydrogenated Castor Oil | 0.20 | 0.300 | 0.20 | 0.20 |
| Ethanol | 2.50 | 1.00 | 2.50 | 2.50 |
| 1,2 propanediol | 1.14 | 0.09 | 1.14 | 1.14 |
| Sodium hydroxide | 4.60 | 3.01 | 4.60 | 4.60 |
| Mono Ethanol Amine | | | | |
| Na Cumene Sulphonate | | | | |
| Silicone emulsion | 0.0030 | 0.0030 | 0.0030 | 0.0030 |
| Dye | 0.002 | 0.00084 | 0.00084 | 0.00084 |
| Opacifier (Styrene Acrylate based) | | | | 0.1 |
| Bentonite Softening Clay | | | | |
| Acrylamide/MAPTAC (ex Nalco Chemicals of Naperville, IL) | | | 0.40 | |
| Mirapol 550 (ex Rhodia Chemie, France) | 0.40 | 0.25 | | |
| Polyquaternium 10 - Cationic hydroxyl ethyl cellulose | | | | 0.30 |

-continued

| Examples of liquid detergents | E | F | G | H |
|---|---|---|---|---|
| PP-5495 (silicone ex Dow Corning Corporation, Midland, MI) | | 3.0 | | |
| DC 1664 (silicone ex Dow Corning Corporation, Midland, MI) | 3.0 | | 3.0 | |
| Pearlescent agent* | | | 0.2 | |
| Perfume micro capsules** (expressed as perfume oil) | 0.9 | 0.3 | 0.5 | 1.2 |
| Perfume | 1.00 | 0.65 | 1.00 | 1.00 |
| Poly Ethylene Imine MW 25000 | | | | |
| Water | Up to 100 | Up to 100 | Up to 100 | Up to 100 |

*Mica-TiO₂ (Prestige Silk Silver Star ex Eckart) or BiOCl (Biron Silver CO-Merck) or pre-crystallized EGDS (Tegopearl N 100 ex Degussa, expressed as pure EGDS)
**Microcapsule added as 35% active slurry (aqueous solution). Core/wall ratio can range from 80/20 up to 90/10 and average particle diameter can range from 5 μm to 50 μm, and can be purified via any of the aforementioned examples.

| Examples of liquid detergents | I | J | K |
|---|---|---|---|
| C14-C15 alkyl poly ethoxylate (8) | 4.00 | 6.1 | |
| C12-C14 alkyl poly ethoxylate (7) | | | 2.00 |
| C12-C14 alkyl poly ethoxylate (3) sulfate Na salt | 6.78 | | |
| Linear Alkylbenzene sulfonate acid | 1.19 | 7.8 | 15.0 |
| Citric Acid | 2.40 | 2.6 | 2.50 |
| C12-C18 Fatty Acid | 4.48 | 2.6 | 11.4 |
| Enzymes | | .55 | .07 |
| Boric Acid | 1.25 | 1.50 | 1.3 |
| Trans-sulphated ethoxylated hexamethylene diamine quat | 0.71 | 1.20 | |
| Diethylene triamine penta methylene phosphonic acid | 0.11 | 0.20 | 0.7 |
| Fluorescent brightener | | 0.09 | 0.14 |
| Hydrogenated Castor Oil | 0.300 | 0.45 | 0.09 |
| Ethanol | 1.00 | 1.40 | 0.7 |
| 1,2 propanediol | 0.09 | 3.30 | 6.7 |
| Sodium hydroxide | 3.01 | 3.00 | 5.5 |
| Mono Ethanol Amine | | 0.50 | |
| Na Cumene Sulphonate | | | 1.6 |
| Silicone emulsion | 0.0030 | 0.0030 | 0.30 |
| Dye | 0.00084 | 0.02 | 0.004 |
| Opacifier (Styrene Acrylate based) | | | |
| Bentonite Softening Clay | | | 3.40 |
| Acrylamide/MAPTAC (ex Nalco Chemicals of Naperville, IL) | | | |
| Mirapol 550 (ex Rhodia Chemie, France) | | | |
| Polyquaternium 10 - Cationic hydroxyl ethyl cellulose | 0.18 | | |
| PP-5495 (silicone ex Dow Corning Corporation, Midland, MI) | | | |
| DC 1664 (silicone ex Dow Corning Corporation, Midland, MI) | 3.0 | | |
| Pearlescent agent* | 0.2 | | |
| Perfume micro capsules (expressed as perfume oil) | 0.2 | 0.45 | 0.75 |
| Perfume | 0.65 | 0.5 | 1.0 |
| Poly Ethylene Imine MW 25000 | | | 0.08 |
| Water | Up to 100 | Up to 100 | Up to 100 |

| Examples of liquid detergents | L | M** | N |
|---|---|---|---|
| C14-C15 alkyl poly ethoxylate (8) | 3.7 | | 20.7 |
| C12-C14 alkyl poly ethoxylate (7) | | 16.7 | |
| C12-C14 alkyl poly ethoxylate (3) sulfate Na salt | 17.8 | | 5.5 |
| Linear Alkylbenzene sulfonate acid | 12.5 | 22.9 | 13.5 |
| Citric Acid | 3.9 | | 1.7 |
| C12-C18 Fatty Acid | 11.1 | 18 | 5.1 |
| Enzymes | 3 | 1.2 | 3 |
| Boric Acid | 0.5 | | 0.5 |
| Trans-sulphated ethoxylated hexamethylene diamine quat | 3.25 | | 1.2 |
| PEI 600 EO20 | 1.25 | | 1.2 |
| Diethylene triamine penta methylene phosphonic acid or HEDP | 1.6 | | 0.85 |
| Fluorescent brightener | 0.2 | 0.3 | 0.14 |
| Hydrogenated Castor Oil | | 0.2 | |
| 1,2 propanediol | 4.3 | 20.3 | 11.7 |
| Sodium hydroxide | | 1.0 | 3.9 |
| Mono Ethanol Amine | 9.8 | 6.8 | 3.1 |
| Dye | Present | Present | Present |
| PDMS | | 2.15 | |
| Potassium sulphite | | 0.2 | |
| Perfume micro capsules* (expressed as perfume oil) | 1.6 | 1.5 | 1.4 |
| Perfume | 1.2 | 1.6 | 1.0 |
| Form. Phenyl Boronic Acid | | | Present |
| Water | Up to 100 | Up to 100 | Up to 100 |

*Microcapsule added as 35% active slurry (aqueous solution). Core/wall ratio can range from 80/20 up to 90/10 and average particle diameter can range from 5 μm to 50 μm, and can be purified via any of the aforementioned examples.
**Low water liquid detergent in Polyvinylalcohol unidose/sachet Example 16

A 25.36% perfume microcapsule slurry was pumped into a hermetic disc stack centrifuge (Alfa Laval model VO194) at 20.1 lbs/min using a positive displacement pump.

The centrifuge was spinning at 5138 rpm with an acting force of 5030 g. The outlet ratios were adjusted to 48:52 (light to heavy) by controlling back pressure on the heavy stream to 28 psig and the light phase was open to atmosphere or 0 psig. The flow of light stream was measured 9.6 lbs/min. and the heavy stream was 10.5 lbs/min. The lights stream solids were measured at 47.66% and heavies at 4.77%. The inlet slurry had a number weighted medium particle size of 4.05 microns. The separated light phase had a number weighted medium particle size of 10.00 microns and the heavy phase had a number weighted medium particle size of 1.43 microns. The perfume content of the incoming slurry was 20.87%. The separated light phase had a perfume content of 44.88% and the heavy phase perfume content was 0.53%. Shell particle removal efficiency was 52.9%

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A benefit agent delivery composition comprising, based on total benefit agent delivery composition weight;
    a.) from about 2% to about 95% of an encapsulated benefit agent;
    b.) from about 1% to about 30% polymeric shell particles, wherein the polymeric shell particles comprise formaldehyde scavenged from the benefit agent delivery composition and act as formaldehyde reservoirs to decrease a level of formaldehyde in the benefit agent delivery composition; and
    c.) the balance of said benefit agent delivery composition being one or more processing aids and carriers.

2. The benefit agent delivery composition of claim 1, wherein said encapsulated benefit agent comprises a benefit agent selected from the group consisting of perfumes; brighteners; insect repellants; silicones; waxes; flavors; vitamins; fabric softening agents; skin care agents; enzymes; anti-bacterial agents; bleaches; and mixtures thereof.

3. The benefit agent delivery composition of claim 1, wherein said formaldehyde scavenged from the benefit agent delivery composition is generated by a reaction of amino resins.

4. The benefit agent delivery composition of claim 1, wherein the encapsulated benefit agent comprises a perfume raw material selected from the group consisting of Quadrant I, II, III and IV perfume raw materials and mixtures thereof.

5. The benefit agent delivery composition of claim 1, wherein said one or more processing aids are selected from the group consisting of water, aggregate inhibiting materials, soil suspending polymers, and mixtures thereof.

6. The benefit agent delivery composition of claim 1, wherein said one or more carriers is selected from the group consisting of polar solvents, and mixtures thereof.

7. The benefit agent delivery composition of claim 6, wherein:
    a. said perfume comprises a perfume raw material selected from the group consisting of Quadrant I, II, III and IV perfume raw materials and mixtures thereof;
    b. said one or more processing aids are selected from the group consisting of water, aggregate inhibiting materials such as divalent salts, soil suspending polymers and mixtures thereof; and
    c. said one or more carriers is selected from the group consisting of water, ethylene glycol, propylene glycol, polyethylene glycol, glycerol, nonpolar solvents, and mixtures thereof.

8. A benefit agent delivery composition made by a process comprising the process of
    separating polymeric shell particles from encapsulated benefit agents in a benefit agent delivery composition under conditions sufficient to reduce the percentage of said polymeric shell particles in said benefit agent delivery composition by at least 20%,
    said separating step being selected from one or more of centrifuging, filtering, solvent exchanging, flash evaporating, decanting, flotation separating, spray drying, reactive adsorbing, reactive absorbing, and electrophoreticly separating,
    wherein the benefit delivery composition comprises one or more encapsulated benefit agents in the absence of added formaldehyde scavenger materials and greater than 01%' polymeric shell particles, said polymeric shell particles comprising a residual by-product of an encapsulation process; and wherein the polymeric shell particles act as formaldehyde reservoirs to decrease a level of formaldehyde in the benefit agent delivery composition.

9. The benefit agent delivery composition of claim 1, wherein said encapsulated benefit agent comprises a sufficient amount of benefit agent to provide, based on total benefit delivery composition weight, from about 1% to about 85% benefit agent.

10. The benefit agent delivery composition of claim 2, wherein the skin care agent comprises paraffins.

11. The benefit agent delivery composition of claim 3, wherein the amino resin comprises one or both of a melamine resin and a urea resin.

12. The benefit agent delivery composition of claim 5, wherein the aggregate inhibiting materials comprise divalent salts.

13. The benefit agent delivery composition of claim 6, wherein the polar solvents are selected from the group consisting of water, ethylene glycol, propylene glycol, polyethylene glycol, glycerol, and mixtures thereof.

14. The benefit agent delivery composition of claim 6 wherein the nonpolar solvents are selected from the group consisting of mineral oil, perfume raw materials, silicone oils, hydrocarbon paraffin oils, and mixtures thereof.

15. The benefit agent delivery composition of claim 7 wherein the nonpolar solvents are selected from the group consisting of mineral oil, perfume raw materials, silicone oils, hydrocarbon paraffin oils, and mixtures thereof.

16. The benefit agent delivery composition of claim 7 wherein the aggregate inhibiting materials comprise divalent salts.

17. The benefit agent delivery composition of claim 1 wherein said encapsulated benefit agent comprises a sufficient amount of benefit agent to provide, based on total benefit delivery composition weight, from about 1% to about 20% benefit agent.

* * * * *